United States Patent
Reinauer et al.

(10) Patent No.: US 9,011,484 B2
(45) Date of Patent: Apr. 21, 2015

(54) MEDICAL INSTRUMENT

(71) Applicants: Josef Reinauer, Sigmaringen (DE); Paul Peschke, Duerbheim (DE)

(72) Inventors: Josef Reinauer, Sigmaringen (DE); Paul Peschke, Duerbheim (DE)

(73) Assignee: Karl Storz GmbH & Co. KG (DE)

( * ) Notice: Subject to any disclaimer, the term of this patent is extended or adjusted under 35 U.S.C. 154(b) by 156 days.

(21) Appl. No.: 13/764,463

(22) Filed: Feb. 11, 2013

(65) Prior Publication Data

US 2013/0211446 A1 Aug. 15, 2013

(30) Foreign Application Priority Data

Feb. 11, 2012 (DE) .......................... 10 2012 002 770

(51) Int. Cl.
*A61B 17/28* (2006.01)
*A61B 17/29* (2006.01)
*A61B 19/00* (2006.01)

(52) U.S. Cl.
CPC .............. *A61B 17/282* (2013.01); *A61B 17/29* (2013.01); *A61B 17/2909* (2013.01); *A61B 19/30* (2013.01)

(58) Field of Classification Search
USPC ................. 606/170–174, 169, 205–208, 113, 606/141–142; 81/427.5, 467, 475, 478, 486
See application file for complete search history.

(56) References Cited

U.S. PATENT DOCUMENTS

| 5,649,955 | A | * | 7/1997 | Hashimoto et al. ........... 606/205 |
| 6,818,005 | B2 | * | 11/2004 | Kupferschmid et al. ..... 606/170 |
| 2012/0004684 | A1 | * | 1/2012 | Reinauer ....................... 606/205 |

FOREIGN PATENT DOCUMENTS

| DE | 19731453 A1 | 2/1999 |
| EP | 0571057 A1 | 11/1993 |
| EP | 2269522 A1 | 1/2011 |

* cited by examiner

*Primary Examiner* — Ryan Severson
*Assistant Examiner* — Anh Dang
(74) *Attorney, Agent, or Firm* — St. Onge Steward Johnston & Reens LLC

(57) ABSTRACT

A medical instrument having a force-limiting apparatus that, upon reaching the borderline force, ensures maintenance of the applied resistance force. It is proposed that the force-limiting apparatus should include a housing in which two components that can move in opposite directions to one another in the longitudinal direction of the housing are disposed in such a way that both components are disposed so that they can slide axially in the housing against the force of at least one spring element disposed in the housing, such that the two components are coupled with one another by at least one force transmission element that is acting on both components.

13 Claims, 4 Drawing Sheets

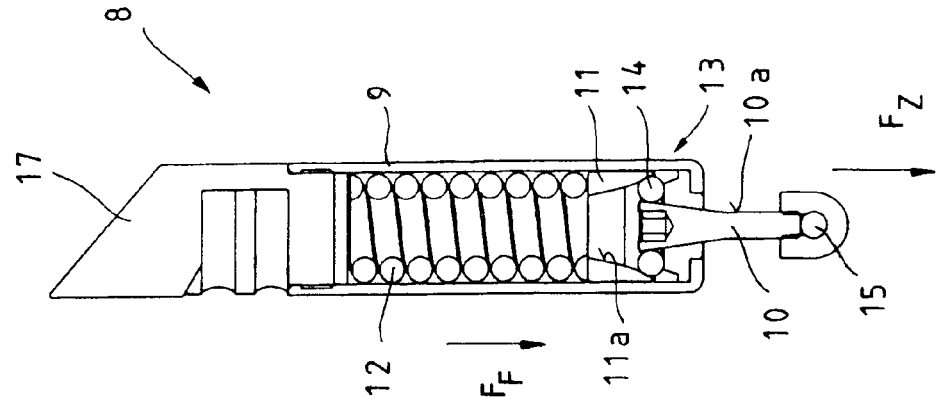
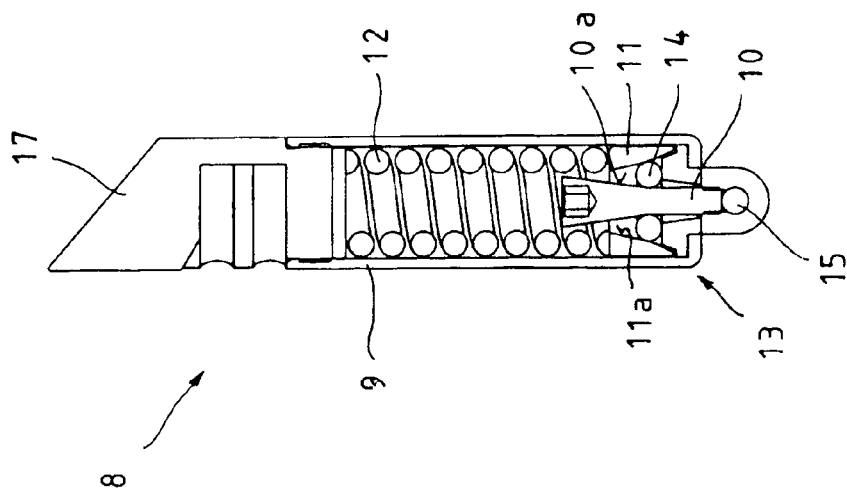

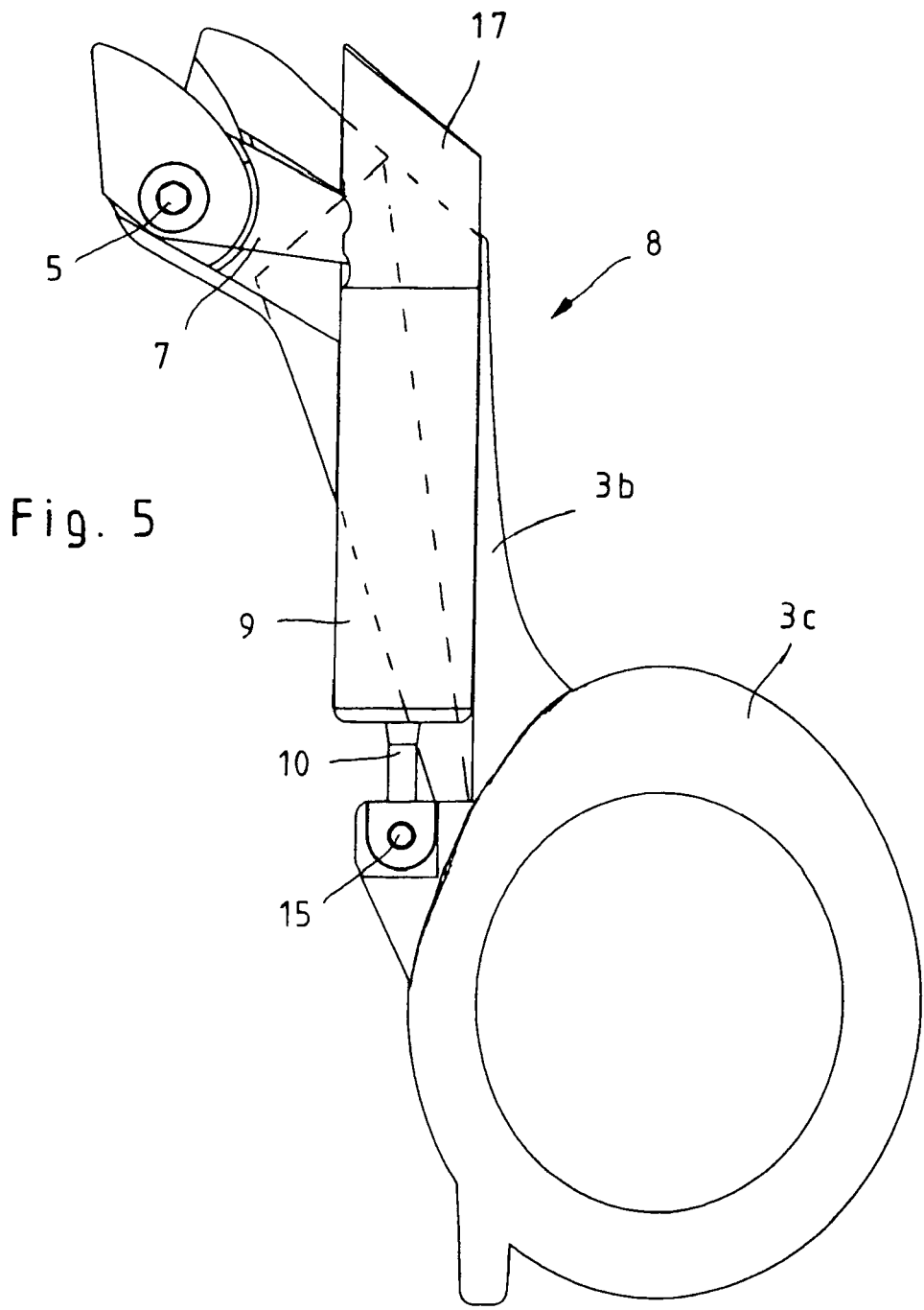

MEDICAL INSTRUMENT

FIELD OF THE INVENTION

The present invention relates to a medical instrument having a shaft on whose distal end a tool is disposed that has at least one movable jaw member and on whose proximal end a handle is disposed that has at least one movable gripping member, such that the movable jaw member and the movable gripping member are operatively linked with one another via a push/pull element and such that, between the movable gripping member and the movable jaw member, at least one reversibly acting force-limiting device is disposed to limit the force transmission from the movable gripping member onto the components that are operatively linked with the movable gripping member.

BACKGROUND OF THE INVENTION

Medical instruments of this type can be, for example, a grasping, holding or dissecting forceps, scissors or similar type of instrument in which a movable tool, for example a pivotable jaw member, is moved by manual force via a displaceable gripping member of the handle.

These known medical instruments, which are used in endoscopic surgery for instance, comprise a shaft on whose distal end a tool is disposed that comprises at least one movable jaw member and on whose proximal end a handle is disposed that is equipped with at least one movable gripping member. Said movable jaw member and said movable gripping member are connected with one another by a push/pull element for opening and closing the movable jaw member. The gripping members of the handles are geometrically configured as a rule in such a way that force exerted by the user's hand on the gripping member is markedly reinforced in transmitting to the push/pull element coupled with the jaw member, for example in a 10:1 ratio, in order to achieve sufficiently high closing power on the jaw member even without great force exertion.

To prevent such great forces from being exerted by the handle on the jaw members and/or the push/pull element, which can lead to damage or even destruction of individual components, it is taught in the art to equip medical instruments with a force-limiting apparatus, which, in the event of exceeding a borderline force, reversibly separates the components that are coupled together.

To do this, it is also familiar in the art to equip the force transmission mechanism with a predetermined breaking point. While this type of force limitation ensures secure protection of the instrument, it has the disadvantage that the instrument is not immediately ready for use again because it must be dismantled in order to repair the predetermined breaking point.

A medical instrument of this type, with a reversibly acting force-limiting apparatus, is known in the art, for example from DE 197 31 453 C2. In this known medical instrument, the force limitation is configured as an elastically reshapable part of the push/pull element that is reversibly reshaped upon exceeding the borderline force.

Also known in the art, from EP 2 269 522 A1, is a generic medical instrument whose force-limiting apparatus is configured in such a way that the force-limiting apparatus, when activated, reduces the force applied by the handle essentially to zero. This known instrument has proved itself thoroughly in practice, but it is advantageous for individual application cases to keep the force exerted by the handle even after exceeding the borderline force.

SUMMARY OF THE INVENTION

It is consequently the object of the invention to provide a medical instrument with a force-limiting apparatus that, upon reaching the borderline force, ensures maintenance of the applied resistance force.

This object is achieved according to the invention in a manner characterized by the totality of the features of Claim 1, and in particular the force-limiting apparatus includes a housing in which two components, which can slide in contrary direction to one another in the longitudinal direction of the housing, are disposed in such a way that both components are positioned to be capable of sliding axially against the force of at least one spring element mounted in the housing, such that the two components are coupled with one another by at least one force transmission element that acts on both components.

The inventive configuration of the force-limiting apparatus with the two components that can slide in opposite directions to one another in the longitudinal direction of the housing has the advantage that the spring-loaded axially slidable components, after reaching a borderline force, are continually pushed toward one another with increasing resistance force by the at least one force transmission element, so that force exerted by the movable gripping member of the handle does not exceed the borderline force and the resistance force is held constant.

According to a first practical embodiment of the invention, it is proposed that the at least one force transmission element, by which the tractive force of the movable gripping member of the handle can be transmitted to the two components, should be configured as a rolling element in the shape of a sphere. This type of force transmission element constitutes a variant that is especially simple to produce and to assemble. Alternatively, said rolling element can also be a roller, needle, drum or cone.

It is further proposed with the invention that the contact surfaces on which the at least one force transmission element is contiguous with both components should be configured as sloping surfaces inclined toward one another in such a way that the borderline force from triggering the force-limiting apparatus is an angular function of the force of the force transmission element onto the sloping contact surface of the first component, such that the force of the force transmission element on the sloping contact surface of the first component is an angular function of the tractive force exerted on the sloping contact surface of the second component by the movable gripping member of the handle.

To dispose the force-limiting apparatus, it is proposed according to a preferred embodiment of the invention that it should be disposed in the movable gripping member of the handle in the area of the force transmission onto the push/pull element. Disposing the force-limiting apparatus in the handle is particularly advantageous in endoscopic instruments because sufficient space is available in such instruments to incorporate such an apparatus because of the slender configuration of the shafts, in particular in the area of the handle.

To configure the force-limiting apparatus, it is proposed according to a practical embodiment of the invention that the one component should be configured as a tension rod mounted on the movable gripping member of the handle and the other component should be configured as a sleeve coaxially surrounding the tension rod when the force-limiting apparatus is in non-triggered position. The at least one spring element is advantageously disposed in the housing of the force-limiting apparatus in such a way that it is directly contiguous with the sleeve and pre-tensed. The pre-tensing contiguous with the sleeve determines the borderline force from which the spring-loaded, axially slidable components are continually slid toward one another as increasing force is exerted by the movable gripping member of the handle.

The contact surface of the tension rod with which the at least one force transmission element is contiguous is configured according to the invention as a cone that tapers to a contact point of the tension rod on the pivotable gripping member and has a flat, preferably non-constant conical angle. The flat conical angle has the effect that, during a movement of the tension rod toward the force transmission element, the force exerted by the tension rod onto the force transmission element exerts a large radial force component onto the force transmission element by means of which said element in turn acts on the contact surface of the sleeve.

The contact surface of the sleeve, with which the at least one force transmission element is contiguous, is configured according to the invention as a cone that widens in trumpet shape toward a contact point of the tension rod on the pivotable gripping member.

The conical angle of the sleeve, which widens in trumpet shape, has the effect that the vertical force component exerted by the force transmission element onto the contact surface becomes greater as the sleeve slides increasingly in the axial direction away from the force transmission element, and thus a greater pressure is exerted onto the spring element that is contiguous with the sleeve. The conical angle increases in moving in the direction of the gripping member and can at first be situated between 10 and 15 degrees and can increase up to about 40 degrees. The cone can have sections with a constant angle as well as sections with a continually increasing angle.

To adjust the medical instrument to various application purposes as well as to adjust to various tool jaw members, the borderline force that causes triggering of the force-limiting apparatus can be adjusted by pre-tensing the at least one spring element.

It is further proposed with the invention that the triggering of the force-limiting apparatus should be optically perceptible in order to indicate to the user without any doubt that the admissible borderline force has been exceeded and the force-limiting apparatus has been triggered.

In addition, a modified embodiment of the invention is proposed in which the force-limiting apparatus limits pressure forces or, in an additional modified embodiment, limits both pressure and tractive forces.

It is finally proposed with an alternative embodiment of the invention that the force-limiting apparatus should be disposed in the area of the push/pull element and should be configured, for example, as a part of the push/pull element.

Additional features and advantages of the invention can be seen from the appended drawings, in which an embodiment of a medical instrument according to the invention is illustrated only by way of example, without restricting the invention to this embodiment.

BRIEF DESCRIPTION OF THE DRAWINGS

FIG. 3 shows an enlarged isolated depiction of the force-limiting apparatus according to FIG. 2.

FIG. 4 shows a depiction according to FIG. 3 but depicting the end position of the force-limiting apparatus.

FIG. 5 shows a non-sectional schematic lateral view of the pivotable gripping member with triggered force-limiting apparatus.

DETAILED DESCRIPTION OF THE INVENTION

Figure 1:
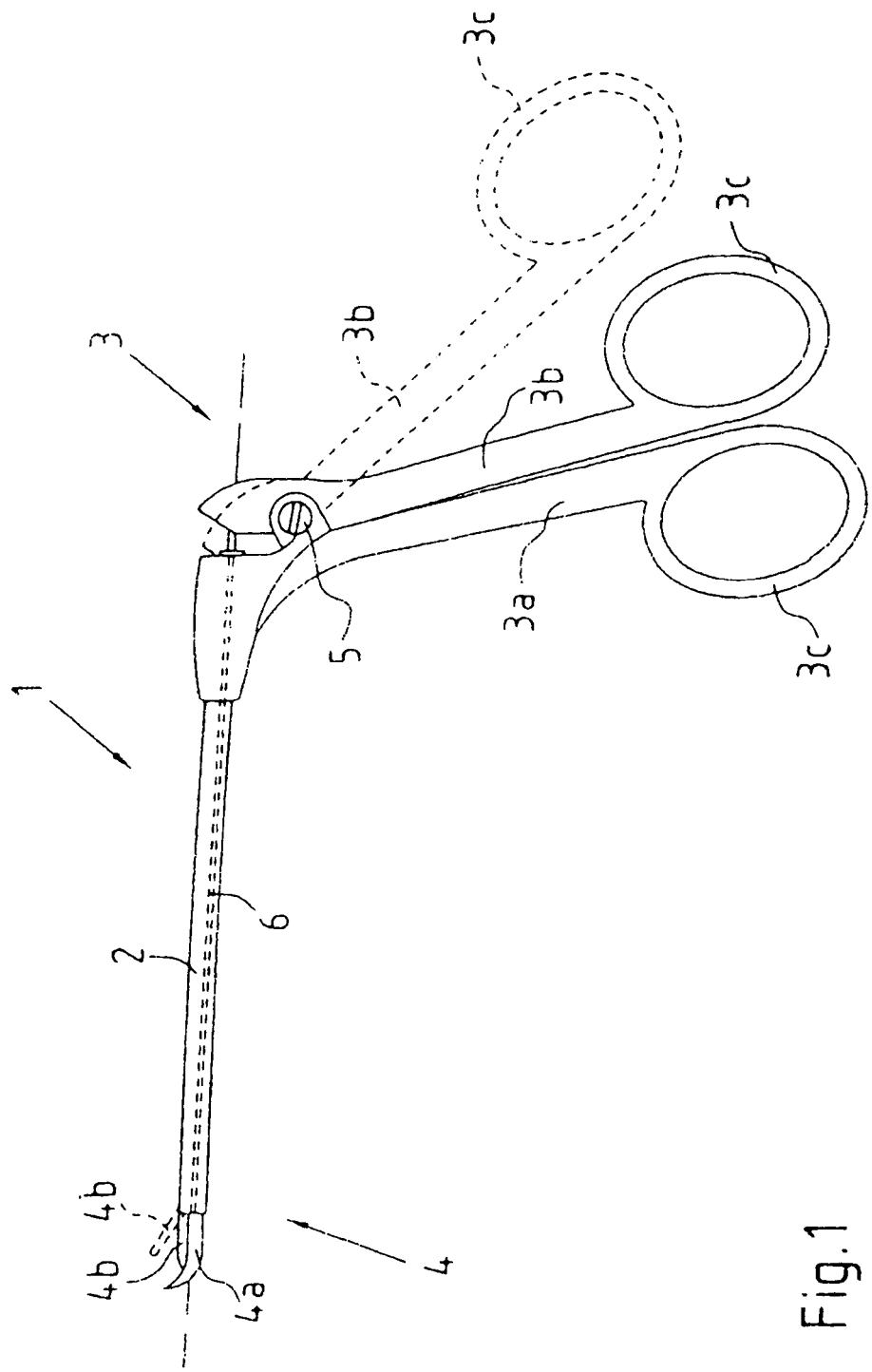
FIG. 1 shows a schematic lateral view of an inventive medical instrument.

The drawing in FIG. 1 schematically shows a medical instrument 1, which can take the form, for example, of a grasping, holding, or dissecting forceps, scissors, or similar instrument, which is moved by hand pressure on a tool, for example a pivotable jaw member.

The medical instrument 1, illustrated only schematically, consists essentially of a hollow shaft 2 on whose proximal end a handle 3 is disposed, which consists of a rigid gripping member 3a and a gripping member 3b that can pivot with respect to the rigid gripping member 3a. On the distal end of the shaft 2 a tool 4 is disposed that consists of a rigid jaw member 4a and a jaw member 4b that can pivot with respect to the rigid jaw member 4a. Which of the two gripping members 3a or 3b of the handle 3 is configured as pivotable or otherwise movable, is not relevant for the manner of functioning of the medical instrument 1.

As can further be seen from FIG. 1, the pivotable jaw member 4b of the tool 4 and the gripping member 3b of the handle 3, which can pivot about a pivot axis 5, are operatively linked with one another by a push/pull element 6, which is disposed to be axially slidable in the hollow shaft 2, in such a way that moving the gripping member 3b of the handle 3 converts the pivotable jaw member 4b of the tool 4 from the closed position (shown in solid lines in FIG. 1) into the opened position (shown in dotted lines in FIG. 1) or vice versa. The relevant position of the pivotable gripping member 3b of the handle 3 is likewise shown in solid lines in FIG. 1 (for closed position) and in dotted lines (for opened position).

Figure 2:
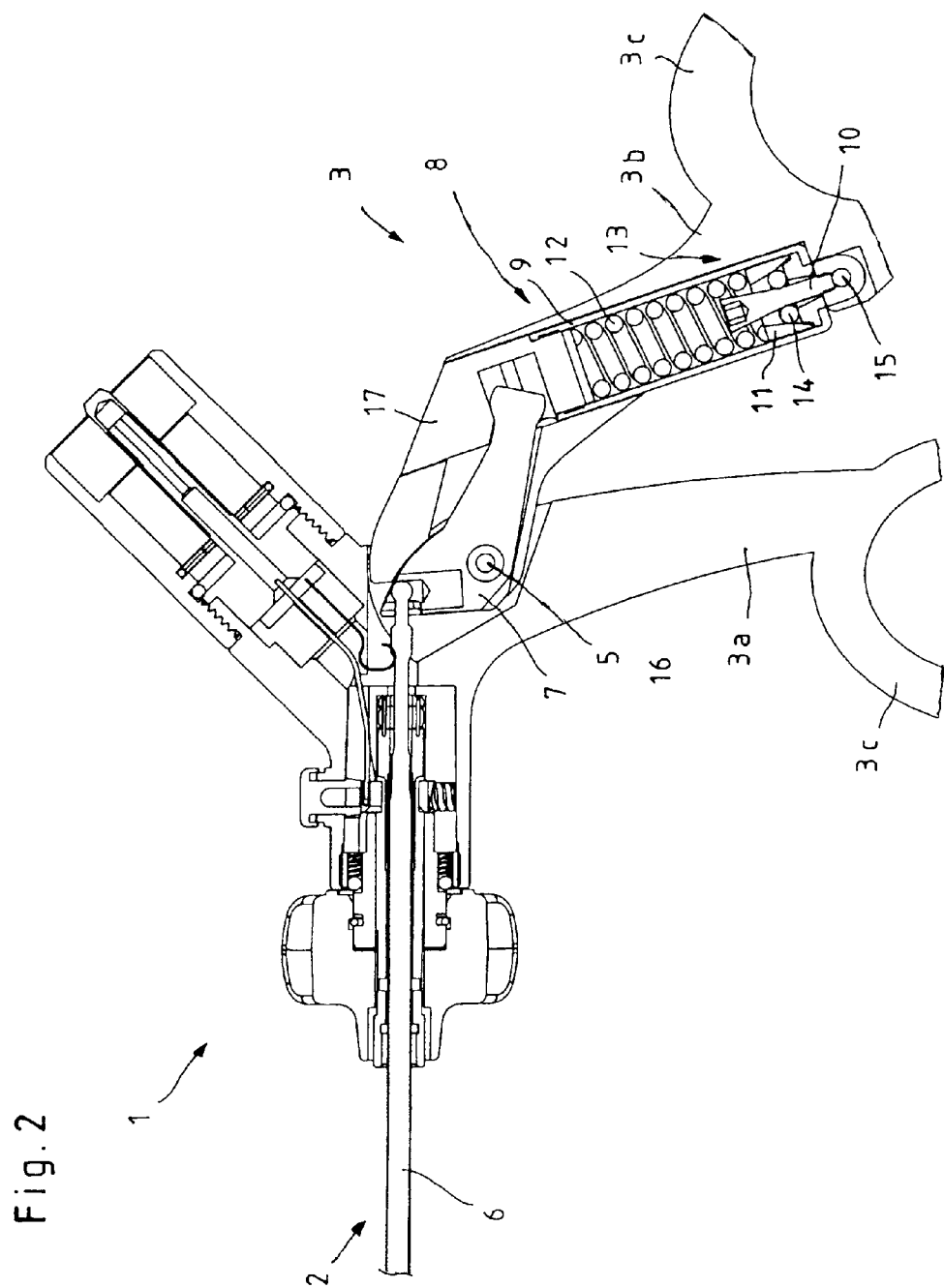
FIG. 2 shows an enlarged and partly sectional schematic depiction of the handle of a medical instrument according to FIG. 1, showing the force-limiting apparatus in non-triggered condition.

As can be seen from a comparison of FIGS. 1 and 2, the pivotable gripping member 3b is connected by a rocker arm 7 with the axially slidable push/pull element 6 and the distance from the pivot axis 5 to the site at which the rocker arm 7 is connected with the axially slidable push/pull element 6 is substantially shorter than the distance from the pivot axis 5 to the finger loop 3c disposed on the farthest proximal end of the gripping member 3b. The gear ratio is approximately 10:1, so that the closing force exerted by the user's hand is reinforced tenfold.

To prevent the handle 3 from exerting such great forces on the jaw members 4a and 4b and/or the push/pull element 6 as could result in damage or even destruction of individual components, the medical instrument 1 comprises a force-limiting apparatus 8, which upon exceeding a borderline force reversibly limits the transmitted force, ensuring that the force acting on the tool 4 is held constant even with increasing force being exerted on the pivotable gripping member 3b.

In the illustrated embodiment of the medical instrument 1, the force-limiting apparatus 8, as can be seen from FIGS. 2 and 5, is disposed in the movable gripping member 3b of the handle 3 in the area of the force transmission to the push/pull element 6.

Alternatively to the illustrated arrangement of the force-limiting apparatus 8 in the handle 3, it is also possible to dispose the force-limiting apparatus 8 in the area of the push/pull element 6 and to configure it, for example, as part of the push/pull element 6.

The structure and functioning of the force-limiting apparatus 8 can be seen from the drawings in FIGS. 2 through 5.

The force-limiting apparatus 8 consists essentially of a housing 9 in which two components 10 and 11, which can slide in opposite directions to one another in the longitudinal direction of the housing 9, are disposed in such a way that both components 10 and 11 are disposed to be axially slidable in the housing 9 against the force of at least one spring element 12 disposed in the housing 9, such that said components 10 and 11 are coupled together by means of at least one force transmission element 13 that acts on both components 10 and 11 and transmits the tractive force FZ of the movable gripping member 3b of the handle 3 onto both components 10 and 11.

As can be seen in particular from FIGS. 3 and 4, the contact surfaces 10a and 11a of the two components 10 and 11, on which the force transmission element 13 is contiguous with both components 10 and 11, are configured as sloping surfaces inclined toward one another.

The at least one force transmission element 13, which is contiguous with the contact surfaces 10a and 11a, is configured as a sphere 14 in the embodiment illustrated in FIGS. 2 through 4.

As can further be seen from FIGS. 2 through 4, the two components 10 and 11, which are slidable in opposite directions to one another and are disposed in the housing 9 of the force-limiting apparatus 8, are configured as a tension rod 10 disposed on the movable gripping member 3b of the handle 3 and as a sleeve 11 that essentially coaxially surrounds the tension rod 10. Transmission of tractive force FZ of the movable gripping member 3b of the handle 3 by the force transmission element 13 onto the two components 10 and 11 occurs via the tension rod 10, which is disposed at a contact point 15 on the movable gripping member 3b of the handle 3. The spring element 12 in this embodiment is pre-tensed on the side turned away from the tension rod 10 and is directly contiguous with the sleeve 11.

In the illustrated embodiment, six spheres 14 are foreseen as force transmission elements 13 and are contiguous with the corresponding contact surfaces 10a and 11a of the tension rod 10 as well as of the sleeve 11.

The contact surface 10a of the tension rod 10, with which the spheres 14 are contiguous, is configured as a cone with flat conical angle that tapers toward the contact point 15 of the tension rod 10 on the pivotable gripping member 3b. The flat conical angle has the effect that, upon a movement of the tension rod 10 toward the spheres 14, the force exerted by the tension rod 10 on the spheres 14 exerts a great radial force component on the spheres 14, with which they in turn act on the contact surface 11a of the sleeve 11.

The contact surface 11a of the sleeve 11, with which the spheres 14 are contiguous, is configured as a cone that widens in trumpet shape toward the contact point 15 of the tension rod 10 on the pivotable gripping member 3b. The conical angle of the sleeve 11, widening in trumpet shape, has the effect, after reaching a borderline force, that the vertical force component exerted by the spheres 14 onto the contact surface 11a becomes greater with increased sliding of the sleeve 11 in the axial direction away from the force transmission element (upwards, in FIGS. 3 and 4) and thus exerts a greater pressure force on the spring element 12 contiguous with the sleeve 11. The conical angles of the tension rod 10 and sleeve 11 are designed so that the pressure force on the spring element 12 contiguous with the sleeve 11 compensates for the force of the spring element 12 that increases according to the spring constant.

Because of the conical configuration of the support surfaces 10a and 11a, the counter-force of the force-limiting apparatus 8 acting against the spring force FF of the spring element 12 is an angular function of the force of the force transmission element 13 on the sloping support surface 11a of the sleeve 11, such that the force of the force transmission element 13 on the sloping support surface 11a of the sleeve 11, for its part, is an angular function of the tractive force FZ exerted by the movable gripping member 3b of the handle 3 on the sloping support surface 10a of the tension rod 10.

The illustrated force-limiting apparatus 8 operates as follows:

When the pivotable gripping member 3b of the handle 3 pivots about the pivot axis 5, the tension rod 10, which is connected at the contact point 15 and mounted in the housing 9, is moved with it and, as a result of the exerted tractive force FZ, counteracts the pre-tensing of the spring element 12, interposing the spheres 14 as well as the sleeve 11, while the housing 9 follows the movement of the tension rod.

As a result of this movement, the rocker arm 7, which is suspended at the upper end of the housing 9 and can pivot about the pivot axis 5, is pivoted and pulls the push/pull element 6 in the proximal direction by a form-locked suspension to close the pivotable jaw member 4b of the tool 4.

If at this point, for example by gripping an object with the jaw members 4a and 4b of the tool 4, the pivotable jaw member 4b cannot be closed further and thus the push/pull element 6 likewise cannot be pulled farther in the proximal direction, then, because of the mounting of the rocker arm 7 on the housing 9, the tractive force FZ on the housing increases and exceeds the spring force FF exerted by the pre-tensing of the spring element 12.

Additional withdrawal of the rocker arm 10 from the housing 9 of the force-limiting apparatus 8, because of the conical contact surface 10a of the rocker arm 10, causes additionally increasing pressure force on the spheres 14 that serve to transmit force onto the sleeve 11. Because of the flat conical angle of the contact surface 10a of the rocker arm 10 on the spheres 14, the pressure force exerted by the rocker arm 10 on the spheres 14 has a very high radial force component.

This strong radial force component, with which the spheres 14 in turn act on the contact surface 11a of the sleeve 11, because of the downward trumpet-shaped widening of the contact surface 11a of the sleeve 11, causes on the spheres 14 a continual rise in the vertical force component exerted by the spheres 14 on the sleeve 11 and thus a compression of the spring element 12 while the entire length of the force-limiting apparatus 8 increases; that is, the distance from the upper end of the housing 9 to the contact point 15 becomes longer.

The configuration of the force-limiting apparatus 8 with the two components, rocker arm 10 and sleeve 11, that can slide in opposite directions to one another in the longitudinal direction of the housing 9 and are operatively linked with one another by the spheres 14 that are contiguous with the bilateral conical contact surfaces 10a and 11a and serve for force transmission, has the effect that the spring-loaded axially slidable components 10 and 11 until they reach an end stop 16 are continually pushed against one another by the spheres 14 with increasing resistance force, so that the force exerted by the movable gripping member 3b of the handle 3 does not exceed the borderline force and the resistance force is held constant.

Withdrawing the rocker arm 10 after exceeding the borderline force causes an extension of the pivot path of the pivotable gripping member 3b until reaching an end stop 16, so that further movement of the pivotable gripping member 3b remains without impact on the tool 4 at the distal end.

The acquired spring tension of the spring element 12 is sufficient, upon pivoting back the pivotable gripping member 3b into the starting position according to FIG. 2, to return the sleeve 11 as well as the spheres 14 reversibly back into the starting position so that the force-limiting apparatus 8 is again ready for use.

In the embodiment depicted in FIGS. 2 through 5, the force-limiting apparatus 8 is additionally equipped with a cap 17, which upon releasing the force-limiting apparatus 8 moves out of the pivotable gripping member 3b of the handle 3 because the pivotable gripping member 3b can be moved again after reaching the borderline force, without causing a more extensive tipping movement of the rocker arm 7. The user is thereby informed of the exceeding of the borderline force and the release of the force-limiting apparatus 8, as can be seen from FIG. 5.

The force-limiting apparatus 8 according to the described embodiment is designed to limit tractive forces. To be able to limit pressure forces, modifications are continually required so that the length of the force-limiting apparatus 8 decreases upon exceeding the borderline force. For this purpose the rocker arm 10 can be replaced with a pressure bolt whose iconicity decreases starting from a contact point, along with the use of a sleeve with a iconicity set against the sleeve 11. Depending on the spatial arrangement of the sleeve, it is possible, instead of the pressing spring element 12, to use a tractive spring, which is connected both with the housing and with the sleeve. In order to be able to limit both tractive and pressure forces, a combined push/pull anchor must be used that interacts with two sleeves 11 and spring elements 12 opposite to one another.

A medical instrument 1 configured in this way is characterized in that the reversibly acting force-limiting apparatus 8 maintains a residual resistance force even after reaching the borderline force.

What is claimed is:

1. A medical instrument comprising:
a shaft on whose distal end a tool is disposed that includes at least one movable jaw member and on whose proximal end a handle is disposed that is equipped with at least one movable gripping member, such that the at least one movable jaw member and the at least one movable gripping member are operatively linked by a push-pull element and such that, between the at least one movable gripping member and the at least one movable jaw member at least one reversibly acting force-limiting apparatus is disposed to limit a force that is transmitted by force transmission from the at least one movable gripping member onto the at least one movable jaw member and the push-pull element, that are operatively linked with the at least one movable gripping member, characterized in that the at least one reversibly acting force-limiting apparatus includes a housing in which two components, which can slide in opposite directions to one another in a longitudinal direction of the housing, are disposed in such a way that both components are disposed so that they can slide axially in the housing against a force of at least one spring element, such that the two components are coupled together by at least one force transmission element configured as a sphere acting on both components, wherein the at least one force transmission element is contiguous with two contact surfaces of the two components, the two contact surfaces configured as sloping surfaces inclined toward one another.

2. The medical instrument according to claim 1, wherein a tractive force of the at least one movable gripping member of the handle can be transmitted onto the two components by the at least one force transmission element.

3. The medical instrument according to claim 1, wherein the at least one reversibly acting force-limiting apparatus is disposed in the at least one movable gripping member of the handle in the area of a force transmission mechanism on the push-pull element.

4. The medical instrument according to claim 1, wherein a limiting load that causes triggering of the at least one reversibly acting force-limiting apparatus can be adjusted by the at least one spring element.

5. The medical instrument according to claim 4, wherein a pre-tensing of the at least one spring element corresponds to the limiting load.

6. The medical instrument according to claim 1, wherein a triggering of the at least one reversibly acting force-limiting apparatus can be perceived optically.

7. The medical instrument according to claim 1, wherein the at least one reversibly acting force-limiting apparatus, in the event of triggering, keeps a tractive force applied by the at least one movable gripping member of the handle essentially constant.

8. The medical instrument according to claim 1, wherein the at least one reversibly acting force-limiting apparatus is disposed in an area of the push-pull element.

9. A medical instrument comprising: a shaft on whose distal end a tool is disposed that includes at least one movable jaw member and on whose proximal end a handle is disposed that is equipped with at least one movable gripping member, such that the at least one movable jaw member and the at least one movable gripping member are operatively linked by a push-pull element and such that, between the at least one movable gripping member and the at least one movable jaw member at least one reversibly acting force-limiting apparatus is disposed to limit a force that is transmitted by force transmission from the at least one movable gripping member onto the at least one movable jaw member and the push-pull element, that are operatively linked with the at least one movable gripping member, characterized in that the at least one reversibly acting force-limiting apparatus includes a housing in which two components, which can slide in opposite directions to one another in a longitudinal direction of the housing, are disposed in such a way that both components are disposed so that they can slide axially in the housing against a force of at least one spring element, such that the two components are coupled together by at least one force transmission element acting on both components, wherein one of the components is configured as a rocker arm disposed on the at least one movable gripping member of the handle and the other of the two components is configured as a sleeve that essentially coaxially surrounds said rocker arm.

10. The medical instrument according to claim 9, wherein the at least one spring element is directly contiguous with the sleeve.

11. The medical instrument according to claim 9, wherein the contact surface of the rocker arm, with which the at least one force transmission element is contiguous, is configured as a cone with a flat conical angle, which tapers to a contact point of the rocker arm on the at least one pivotable gripping member.

12. The medical instrument according to claim 9, wherein the contact surface of the sleeve, with which the at least one force transmission element is contiguous, is configured as a cone that widens in trumpet shape to a contact point of the rocker arm on the at least one pivotable gripping member.

13. The medical instrument according to claim 9, wherein a borderline force starting from which the at least one reversibly acting force-limiting apparatus is triggered, is an angular function of a force of the at least one force transmission element on a sloping contact surface of the sleeve, such that the force of the at least one force transmission element on the sloping contact surface of the sleeve is an angular function of a tractive force exerted on a sloping contact surface of the rocker arm by the at least one movable gripping member of the handle.

\* \* \* \* \*